(12) United States Patent
Kasuya et al.

(10) Patent No.: US 9,982,369 B2
(45) Date of Patent: May 29, 2018

(54) FIBER AND COLUMN FOR PROTEIN ADSORPTION

(71) Applicant: Toray Industries, Inc., Tokyo (JP)

(72) Inventors: Junichi Kasuya, Otsu (JP); Naotoshi Tomita, Otsu (JP); Yoshiyuki Ueno, Otsu (JP)

(73) Assignee: Toray Industries, Inc. (JP)

( * ) Notice: Subject to any disclaimer, the term of this patent is extended or adjusted under 35 U.S.C. 154(b) by 0 days. days.

(21) Appl. No.: 15/511,185

(22) PCT Filed: Sep. 16, 2015

(86) PCT No.: PCT/JP2015/076292
§ 371 (c)(1),
(2) Date: Mar. 14, 2017

(87) PCT Pub. No.: WO2016/043223
PCT Pub. Date: Mar. 24, 2016

(65) Prior Publication Data
US 2017/0253999 A1 Sep. 7, 2017

(30) Foreign Application Priority Data

Sep. 16, 2014 (JP) .................. 2014-187681

(51) Int. Cl.
| | |
|---|---|
| *D01F 8/06* | (2006.01) |
| *A61M 1/36* | (2006.01) |
| *B01J 20/26* | (2006.01) |
| *B01J 20/28* | (2006.01) |
| *B01J 20/281* | (2006.01) |
| *B01J 20/30* | (2006.01) |
| *C08L 25/06* | (2006.01) |
| *C08L 23/12* | (2006.01) |
| *C08J 7/14* | (2006.01) |
| *D06M 13/392* | (2006.01) |
| *D06M 11/55* | (2006.01) |
| *D06M 13/13* | (2006.01) |
| *A61L 31/04* | (2006.01) |
| *B01D 15/08* | (2006.01) |
| *D06M 101/20* | (2006.01) |

(52) U.S. Cl.
CPC .............. *D01F 8/06* (2013.01); *A61L 31/041* (2013.01); *A61M 1/3679* (2013.01); *B01D 15/08* (2013.01); *B01J 20/267* (2013.01); *B01J 20/281* (2013.01); *B01J 20/28023* (2013.01); *B01J 20/3085* (2013.01); *C08J 7/14* (2013.01); *C08L 23/12* (2013.01); *C08L 25/06* (2013.01); *D06M 11/55* (2013.01); *D06M 13/13* (2013.01); *D06M 13/392* (2013.01); *B01J 2220/52* (2013.01); *C08L 2203/02* (2013.01); *C08L 2203/12* (2013.01); *C08L 2205/025* (2013.01); *C08L 2205/03* (2013.01); *D06M 2101/20* (2013.01); *D06M 2400/01* (2013.01); *D10B 2509/00* (2013.01)

(58) Field of Classification Search
CPC ....... D01F 8/06; A61L 31/041; A61M 1/3679; B01D 15/08; B01J 20/267
USPC .......................................... 502/402
See application file for complete search history.

(56) References Cited

U.S. PATENT DOCUMENTS

2014/0206818 A1 7/2014 Tomita et al.

FOREIGN PATENT DOCUMENTS

| | | |
|---|---|---|
| JP | 49-130969 | 12/1974 |
| JP | 2002-363116 A | 12/2002 |
| JP | 2006-272075 A | 10/2006 |
| JP | 2008-237893 A | 10/2008 |
| JP | 2012-5827 A | 1/2012 |
| WO | 2013/022012 A1 | 2/2013 |

*Primary Examiner* — Edward Johnson
(74) *Attorney, Agent, or Firm* — DLA Piper LLP (US)

(57) ABSTRACT

A fiber for protein adsorption has a water absorption percentage of 1 to 50%, and the fiber includes a polymer containing as repeat units an aromatic hydrocarbon or a derivative thereof, wherein part of aromatic rings contained in the repeat units are cross-linked through a structure represented by Formula (I). A column for protein adsorption uses the fibers. A in Formula (I) is selected from an alkyl aliphatic group, phenyl aromatic group and amino group.

(I)

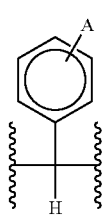

20 Claims, No Drawings

FIBER AND COLUMN FOR PROTEIN ADSORPTION

TECHNICAL FIELD

This disclosure relates to a fiber for protein adsorption and a column for protein adsorption that can be favorably used for adsorption of substances to be adsorbed from protein-containing liquids to be processed such as blood and blood components.

BACKGROUND

Besides dialysis, blood purification therapy known as apheresis has become popular as a treatment in which a liquid to be processed such as blood is removed from the body, and a pathogenic substance or the like in the liquid to be processed is returning the liquid into the body. Known examples of the apheresis therapy include simple plasma exchange; double filtration plasmapheresis; plasma adsorption, in which plasma is separated from blood, and a toxic substance in the plasma is removed; and direct hemoperfusion, in which a toxic substance is directly removed from whole blood.

In plasma adsorption, adsorption columns for adsorptive removal of autoantibodies, and adsorption columns for adsorptive removal of low-density lipoproteins have been practically used. In direct hemoperfusion, adsorption columns for adsorptive removal of endotoxins, and adsorption columns for adsorptive removal of $\beta_2$-microglobulin (hereinafter referred to as $\beta_2$-MG) have been practically used. They are all adsorptive carriers to which a ligand that interacts with the substance to be removed is immobilized.

As a material for adsorption of inflammatory cytokines, a protein-adsorbing carrier in which a ligand having an amino group is immobilized on the surface of a water-insoluble carrier composed of polystyrene or polysulfone has been disclosed (JP 2006-272075 A). A protein-adsorbing carrier in which a ligand having an amino group is immobilized on the surface of a water-insoluble carrier composed of a polyolefin such as polyethylene or polypropylene; a polyester such as polyethylene terephthalate or polybutylene terephthalate; a polysulfone-based polymer such as poly(p-phenylene ether sulfone); a polyetherimide-, polyimide-, polyamide-, polyether-, polyphenylene sulfide-, polystyrene (hereinafter referred to as "PS")-, or polyacrylonitrile-based polymer; or a derivative of any of these macromolecular compounds, or a blended or alloyed product of any of these macromolecular compounds has also been disclosed (JP 2012-5827 A).

A protein-adsorbing carrier prepared by immobilizing a desired functional group on a polymer using an aldehyde or ketone having the functional group has also been disclosed (WO 2013/022012). WO 2013/022012 discloses, as the polymer, those containing an aromatic ring such as polystyrene, polysulfone, polyethersulfone, or polycarbonate.

The disclosed protein-adsorbing carriers are given high adsorption capacities by immobilization of a ligand.

However, in certain kinds of protein-adsorbing carriers, there is a possibility that the physical strength of the carrier decreases due to the process of immobilization of the ligand, causing generation and isolation of particulates from part of the carrier.

In view of this, it could be helpful to provide a fiber for protein adsorption and a column for protein adsorption having high capacity to adsorb a substance to be adsorbed, which are less likely to cause generation of particulates.

SUMMARY

We thus provide a fiber for protein adsorption having the following constitution:

(1) A fiber for protein adsorption,
wherein the fiber has a water absorption percentage of 1 to 50%, and
the fiber comprises a polymer containing as repeat units an aromatic hydrocarbon and/or a derivative thereof, wherein part of aromatic rings contained in the repeat units are cross-linked through a structure represented by Formula (I):

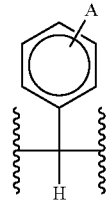

(I)

wherein A is selected from an aliphatic group, aromatic group, and amino group, and each wavy line represents a position bound to an aromatic ring.

Preferably, there are the following constitutions:

(2) The fiber for protein adsorption according to (1), wherein, in the formula, A represents Formula (A-1), (A-2), or (A-3):

(A-1)

(A-2)

(A-3)

wherein $R^1$ to $R^5$ each independently represent a hydrogen atom or a $C_1$-$C_{10}$ hydrocarbon group, and each wavy line represents a binding position.

(3) The fiber for protein adsorption according to (1) or (2), wherein the polymer is a polymer selected from the group consisting of polystyrene, polysulfone, and derivatives thereof (4) The fiber for protein adsorption according to any one of (1) to (3), wherein the single yarn diameter of the fiber is 0.1 to 1000 μm.

(5) The fiber for protein adsorption according to any one of (1) to (4), wherein the number of aromatic rings shown in Formula (I) with respect to the total number of aromatic rings contained in the cross-linked polymer is 4 to 70%.

(6) The fiber for protein adsorption according to any one of (1) to (5), which is for cytokine adsorption.

In terms of usage of the fiber for protein adsorption, a column for protein adsorption comprising, as an adsorptive carrier, the fiber for protein adsorption according to any one of (1) to (6) is provided.

The fiber for protein adsorption and the column for protein adsorption have high capacity to adsorb substances to be adsorbed and can reduce generation of particulates from the fiber. They can thus be favorably used for adsorptive removal of proteins such as I3$_2$-MG and cytokines from protein-containing liquids to be processed such as blood, body fluids from living bodies, and drainages from living bodies.

DETAILED DESCRIPTION

The fiber for protein adsorption has a water absorption percentage of 1 to 50%. This fiber comprises a polymer (hereinafter referred to as "polymer B") containing as repeat units an aromatic hydrocarbon and/or a derivative thereof, wherein part of aromatic rings contained in the repeat units are cross-linked through a structure represented by Formula (I):

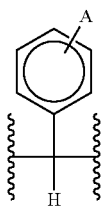

(I)

wherein A is selected from an aliphatic group, aromatic group, and amino group, and each wavy line represents a position bound to an aromatic ring contained in the polymer.

A in the formula is preferably Formula (A-1), (A-2), or (A-3):

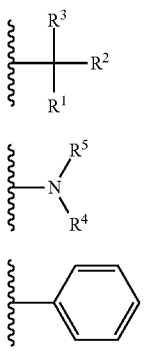

(A-1)

(A-2)

(A-3)

wherein $R^1$ to $R^5$ each independently represent a hydrogen atom or a $C_1$-$C_{10}$ hydrocarbon group, and each wavy line represents a binding position.

The "polymer containing as repeat units an aromatic hydrocarbon and/or a derivative thereof" (hereinafter referred to as "polymer C") means a polymer having a repeat unit in which an aromatic hydrocarbon or a derivative thereof is contained. When the aromatic hydrocarbon is a benzene ring, the polymer has a benzene skeleton in the repeat unit or a side chain thereof. The polymer C may be either a homopolymer or a copolymer.

Examples of the "aromatic hydrocarbon or a derivative thereof" include the following:
  benzene, naphthalene, and anthracene, which are hydrocarbon-group aromatic rings;
  furan, thiophene, and pyrrole, which are aromatic heterocycles; and
  azulene and cyclopentadiene, which are nonbenzenoid aromatic rings.

Among these, a benzene ring is preferred. The polymer C is preferably polystyrene, polysulfone, or a derivative thereof. Copolymers of polystyrene structural units or polysulfone structural units with other structural units may also be used. The copolymer may be either a random copolymer or a block copolymer. The polymer C does not necessarily need to be of a single type, and two or more types of polymers having different structures may be used. Examples of the polymer containing as repeat units a derivative of an aromatic hydrocarbon include styrene-based polymers such as poly(a-methylstyrene) and poly(styrene-divinylbenzene); and polymers having a sulfone group such as polyethersulfone, polyarylethersulfone, and polyphenylsulfone.

The polymer C, which is a material of the polymer B, preferably has a weight average molecular weight of 10,000 to 1,000,000. The polymer C more preferably has a weight average molecular weight of 100,000 to 500,000. The weight average molecular weight herein is calculated in teams of polystyrene as measured by gel permeation chromatography at 40° C. using tetrahydrofuran as a solvent.

The term "part of aromatic rings contained in the repeat unit are cross-linked through a structure represented by Formula (I)" means a state where an aromatic ring contained in a polymer C molecule is covalently linked to an aromatic ring contained in another polymer C molecule through a structure represented by Formula (I) to form a chemical crosslink between the polymer C molecules.

The functional group A is an aliphatic group, aromatic group, or amino group. In the formula, A may be linked to a plurality of aromatic rings. In an aliphatic group, its carbon number is preferably 1 to 31. In an aromatic group, its carbon number is preferably 6 to 10. In an amino group, its carbon number is preferably 0 to 20. Due to the presence of the functional group A defined above, the structure of Formula (I) becomes bulky and, therefore, the desired effect increases. Linking of an aromatic group further increases the effect.

The functional group A is preferably one or more selected from Formulae (A-1), (A-2), and (A-3), wherein $R^1$ to $R^5$ each independently represent a hydrogen atom or a $C_1$-$C_{10}$ hydrocarbon group.

The functional group represented by Formula (A-1) is preferably an isopropyl group or a tert-butyl group. The functional group represented by Formula (A-2) is preferably a diethylamino group.

For adsorption of protein to a fiber, the chemical structure as well as the physical structure of the fiber are important. In the process of adsorption of protein to a fiber surface, the adsorption of the protein is more likely to occur when, for example, a flexible layer is formed on the fiber surface. However, in general, for formation of the flexible surface on the fiber surface, hydrophilicity of the fiber surface is increased. When the fiber has high hydrophilicity, mobility of the polymer present on the fiber surface increases in the liquid so that the protein becomes less likely to be adsorbed on the surface and, furthermore, the physical strength of the fiber decreases, easily causing generation of particulates.

We discovered that fibers having a water absorption percentage of 1 to 50% wherein aromatic rings of one or more types of polymers containing as repeat units an aromatic hydrocarbon and/or a derivative thereof are covalently linked to each other through a structure represented by Formula (I) are useful for adsorption of protein. In the process of adsorption of protein to the fiber surface, a high water absorption percentage of the fiber allows formation of a flexible molecular layer on the fiber surface. On the other hand, when, for example, hydrophilicity of the fiber surface is increased, or mobility of the polymer present on the fiber surface is increased, protein is less likely to be adsorbed. However, when aromatic rings of the polymer(s) are linked to each other through a structure represented by Formula (I) such that the water absorption percentage is 1 to 50%, the fiber surface has improved hydrophobicity due to the aromatic ring contained in Formula (I), and is cross-linked through the structure represented by Formula (I) to form a three-dimensional network structure. Since, by this, a flexible molecular layer is formed on the fiber even without chemically increasing the hydrophilicity, the generation of particulates from the fiber can be reduced. Moreover, since this allows easier interaction of the fiber with protein, the protein adsorption capacity increases.

In the polymer B for the fiber for protein adsorption, not all aromatic rings contained in the polymer C need to be cross-linked. The ratio of the number of aromatic rings contained in the structure represented by Formula (I) to the total number of aromatic rings in the polymer B is preferably 4 to 70%, more preferably 20 to 50%.

When this ratio is too low, the water absorption percentage tends to be high, so that swelling of the fiber is likely to occur. This leads to decreased fiber strength and, hence, to an increase in the particulates generated from the fiber. On the other hand, when the ratio is too high, the water absorption percentage is low, so that the flexible molecular layer on the fiber surface is thin. The protein adsorption capacity is therefore low.

Preferably, for the covalent bonding of aromatic rings in the Polymer C through the structure represented by Formula (I), aromatic rings having a functional group(s) selected from an alkyl group, phenyl group, hydroxy group, mercapto group, amino group, carboxyl group, aldehyde group, and sulfonyl group are cross-linked through a compound(s) having a benzylaldehyde group. More preferably, a fiber containing a polymer selected from polystyrene- or polysulfone-based polymers and derivatives thereof is subjected to cross-linking of the polymer through a compound having a benzylaldehyde group. By the use of a compound having a benzylaldehyde group, a fiber having a structural unit represented by Formula (I) can be obtained.

To control the water absorption percentage of the fiber, the cross-linking is preferably carried out using, as a cross-linking agent, a compound having a functional group whose reactivity is low. The cross-linking is more preferably carried out using benzylaldehyde to which an aliphatic group such as an alkyl group or an alkylene group, or an aromatic ring is bound. When the cross-linking is carried out using benzylaldehyde to which an electron-donating functional group such as an amino group is bound, the degree of cross-linking is high. However, since the water absorption percentage of the fiber tends to be high, the physical strength of the fiber is low so that the effect to reduce generation of particulates is lower than those obtained with the above-described functional groups. When the cross-linking is carried out using an electron-withdrawing compound having benzylaldehyde to which an electron-withdrawing functional group such as a nitro group is bound, the degree of cross-linking is low.

When a compound such as formaldehyde is used as a cross-linking agent, aromatic rings in the fiber after the cross-linking are not covalently bound to each other through a structure represented by Formula (I). The fiber therefore has a porous structure rather than having a form swollen with water. This is thought to be due to the fact that, since cross-linking with formaldehyde causes less steric hindrance, the degree of corrosion of the material of the fiber surface by the solvent used for the cross-linking reaction increases, resulting in leaching of the non-cross-linked polymer portion.

The solvent used for the cross-linking reaction of the polymer C using the compound having a benzylaldehyde group is preferably a solvent that causes dissolution or swelling of polystyrene- or polysulfone-based polymers which are preferably used as the polymer C. This is because, in this cross-linking reaction, an appropriate level of cross-linking occurs in the molecular structure of the polymer on the fiber surface that has become a low density state due to the dissolution or the swelling caused by the solvent, resulting in formation of a three-dimensional polymer network. Preferred specific examples of the solvent include nitrobenzene, nitropropane, and N-methyl-2-pyrrolidone. An acid is preferably added as a catalyst. The acid added is preferably sulfuric acid.

The fiber for protein adsorption may also contain a polymer other than the polymer B such as polyolefins including polyethylene and polypropylene; polyether ketone; polycarbonate; and aromatic polyesters including polyethylene terephthalate. The ratio of the polymer other than the polymer B to the total polymer in the protein-adsorbing fiber is not limited, and is preferably not more than 80 mass %, more preferably not more than 40 mass %.

By including the polymer other than the polymer B in the fiber, and controlling its amount, the water absorption percentage can be controlled. The amount of the polymer B is preferably 1 to 50 mass %, more preferably 11 to 30 mass % with respect to the total amount of the fiber.

When the fiber diameter of the fiber for protein adsorption is too small, the fiber strength is low. On the other hand, when the fiber diameter is too large, the surface area per fiber weight is small so that the protein adsorption capacity per fiber weight is low. In view of this, the fiber diameter is preferably 0.1 to 1000 µm, more preferably 0.5 to 20 µm.

For example, a cartridge may be packed with the fiber for protein adsorption as an adsorptive carrier, to provide a column for protein adsorption for a body fluid such as blood.

EXAMPLES

Our fibers and columns are described below by way of Examples and Comparative Examples. However, this disclosure is not limited by the Examples.

1. Preparation of Protein-Adsorbing Fibers and Columns:
(1) Preparation of Fibers:

Reference Example 1 Preparation of Fibrous Carrier

Using a mixed polymer of 90 mass % polystyrene (weight average molecular weight, 181,000) and 10 mass % polypropylene as the sea component, and polypropylene as the island component, a sea-island composite fiber with a number of islands of 16, a sea/island ratio of 50/50 mass %, and a fiber diameter of 20 µm was prepared by melt spinning using a composite die. The resulting fiber was further drawn 3.1-fold, and mechanical crimps were given thereto to provide a fiber. The fiber was then woven into a cylindrical shape to obtain a fibrous carrier (with a course density of 58 to 60 mm/50 c as measured in a state where the knitted fabric is longitudinally drawn) (hereinafter referred to as "fibrous carrier A").

The fiber diameter herein means the value obtained by randomly collecting 10 small pieces of samples from the fibrous carrier, taking their photographs using a scanning electron microscope (S-800, Hitachi, Ltd.) at a magnification of 2000, measuring the fiber diameter at 10 positions per photograph (a total of 100 positions), and then calculating the average of the measured values.

Reference Example 2 Preparation of Fibrous Carrier

Using a mixed polymer of 35 mass % polystyrene (weight average molecular weight, 261,000) and 35 mass % polypropylene as the core component, and 30 mass % polystyrene (weight average molecular weight, 261,000) as the sheath component, melt spinning was carried out using a composite die to obtain a coated sea-island composite fiber having a core component in which polystyrene is the sea and polypropylene is the island (number of islands, 16; fiber diameter, 26 µm). The product prepared by the melt spinning was woven into a cylindrical shape to obtain a fiber funning a knitted fabric (with a course density of 95 mm/50 c as measured in a state where the knitted fabric is longitudinally drawn) (hereinafter referred to as "fibrous carrier B").

Reference Example 3 Preparation of Woven Fabric A

The polymer having the following composition was subjected to melt spinning using a composite die at a spinning rate of 800 m/minute and a draw ratio of 3 to obtain a sea-island composite fiber having 36 islands. The island component has a core-sheath structure in its inside.

Core component of the island: polypropylene

Sheath component of the island: 90 mass % polystyrene (weight average molecular weight, 261,000) and 10 mass % polypropylene Sea component: copolymerized polyester containing ethylene terephthalate units as major repeating units, and also containing 5-sodium sulfoisophthalic acid as a copolymerization component at 3 mass % with respect to the copolymerized polyester Mass ratio: core in the island/sheath in the island/sea=45/40/15

After preparation of a non-woven fabric composed of 85 mass % of this fiber and 15 mass % of a polypropylene fiber having a diameter of 20 µm (weight per unit area, 133.7 g/m$^2$), a sheet-shaped polypropylene net (thickness, 0.5 mm; single yarn diameter, 0.3 mm; opening, 2-mm square; weight per unit area, 70.3 g/m$^2$) was sandwiched between two sheets of this non-woven fabric, and needle punching was carried out to obtain a non-woven fabric having a three-layered structure (hereinafter referred to as "PP non-woven fabric").

The PP non-woven fabric was treated with 3 mass % aqueous sodium hydroxide solution at 95° C. to dissolve the sea component, to prepare a non-woven fabric (PSt+PP non-woven fabric) having a core-sheath fiber diameter of 5 µm and a bulk density of 0.02 g/cm$^3$ (hereinafter referred to as "non-woven fabric A").

(2) Ligand-introducing Reaction:

Example 1 Preparation of Protein-Adsorbing Fiber A

At 50° C., 18.1 mL of nitrobenzene, 11.9 mL of sulfuric acid, and 0.8 g of 4-isopropylbenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-isopropylbenzaldehyde (hereinafter referred to as "protein-adsorbing fiber A"). Table 1 shows the structure in which aromatic rings are linked to each other through the functional group.

Example 2 Preparation of Protein-Adsorbing Fiber B

At 50° C., 18.1 mL of nitrobenzene, 11.9 mL of sulfuric acid, and 0.4 g of 4-isopropylbenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-isopropylbenzaldehyde (hereinafter referred to as "protein-adsorbing fiber B"). Table 1 shows the structure in which aromatic rings contained in the protein-adsorbing fiber B are linked to each other through the functional group.

Example 3 Preparation of Protein-Adsorbing Fiber C

At 50° C., 18.1 mL of nitrobenzene, 11.9 mL of sulfuric acid, and 1.6 g of 4-isopropylbenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-isopropylbenzaldehyde (hereinafter referred to as "protein-adsorbing fiber C"). Table 1 shows the structure in which aromatic rings contained in the protein-adsorbing fiber C are linked to each other through the functional group.

Example 4 Preparation of Protein-adsorbing Fiber D

At 50° C., 18.1 mL of nitrobenzene, 11.9 mL of sulfuric acid, and 0.8 g of 4-tert-butylbenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-tert-butylbenzaldehyde (hereinafter referred to as "protein-adsorbing fiber D"). Table 1 shows the structure in which aromatic rings contained in the protein-adsorbing fiber D are linked to each other through the functional group.

Example 5 Preparation of Protein-Adsorbing Fiber E

At 50° C., 18.1 mL of nitrobenzene, 11.9 mL of sulfuric acid, and 1.0 g of 4-diethylaminobenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 50 minutes while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-diethylaminobenzaldehyde (hereinafter referred to as "protein-adsorbing fiber E"). Table 1 shows the structure in which aromatic rings contained in the protein-adsorbing fiber E are linked to each other through the functional group.

Comparative Example 1 Preparation of Protein-Adsorbing Fiber F

At 50° C., 18.1 mL of nitrobenzene, 11.9 mL of sulfuric acid, and 0.15 g of 4-isopropylbenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-isopropylbenzaldehyde (hereinafter referred to as "protein-adsorbing fiber F"). Table 1 shows the structure in which aromatic rings contained in the protein-adsorbing fiber F are linked to each other through the functional group.

Comparative Example 2 Preparation of Protein-Adsorbing Fiber G

At 50° C., 18.1 mL of nitrobenzene, 11.9 mL of sulfuric acid, and 3.0 g of 4-isopropylbenzaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber in which cross-links were formed with 4-isopropylbenzaldehyde (hereinafter referred to as "protein-adsorbing fiber G"). Table 1 shows the structure in which aromatic rings are linked to each other through the functional group.

Comparative Example 3 Preparation of Protein-Adsorbing Fiber H

At 50° C., 18.1 mL of nitrobenzene, 11.9 mL of sulfuric acid, and 1.5 g of 4-dimethylaminobenzaldehyde were mixed together, and the resulting mixture stirred to allow dissolution, to prepare 40 mL of a reaction liquid. In this reaction liquid, 1 g of the non-woven fabric A was immersed, and the reaction allowed to proceed for 1.5 hours while the reaction liquid was kept at 50° C. Subsequently, the reacted non-woven fabric was removed from the reaction liquid, and immersed in 40 mL of nitrobenzene for washing. After removing the non-woven fabric, the non-woven fabric was immersed in methanol for washing and further immersed in water for washing to obtain a non-woven fabric in which cross-links were formed with 4-dimethylaminobenzaldehyde (hereinafter referred to as "protein-adsorbing fiber H"). Table 1 shows the structure in which aromatic rings contained in the protein-adsorbing fiber H are linked to each other through the functional group.

Comparative Example 4 Preparation of Protein-Adsorbing Fiber I

In a mixed solution composed of 50 g of N-methylol-a-chloroacetamide, 400 g of nitrobenzene, 400 g of 98 wt % sulfuric acid, and 0.85 g of paraformaldehyde, 50 g of the fibrous carrier B was immersed, and the reaction allowed to proceed at 4° C. for 1 hour. The fiber after the reaction was immersed in 5 L of ice water at 0° C. to stop the reaction, and the fiber then washed with water, followed by extraction removal of nitrobenzene attached to the fiber using methanol. The resulting fiber was dried under vacuum at 50° C. to obtain 71 g of chloroacetamidomethyl-modified cross-linked polystyrene knitted fabric (hereinafter referred to as "AMPSt knitted fabric").

In 500 mL of dimethylsulfoxide (hereinafter referred to as "DMSO"), 1.5 g of tetraethylene pentamine was dissolved, and 20 g of the AMPSt knitted fabric added with stirring to the resulting solution, followed by allowing the reaction to proceed at 25° C. for 6 hours. The AMPSt knitted fabric after the reaction was washed with 500 mL of DMSO on a glass filter. In 150 mL of a solution prepared by dissolving 1.0 g of parachlorophenylisocyanate in DMSO, 3.0 g of the washed AMPSt knitted fabric was placed, and the reaction allowed to proceed at 25° C. for 1 hour. The knitted fabric was then washed with 60 mL each of DMSO and distilled water on a glass filter, and then with 3 L each of distilled water and physiological saline to obtain a protein-adsorbing fiber (hereinafter referred to as "protein-adsorbing fiber I"). Table 1 shows the structure in which aromatic rings contained in the protein-adsorbing fiber I are linked to each other through the functional group.

Comparative Example 5 Preparation of Protein-Adsorbing Fiber J

At 50° C., 18.1 mL of nitrobenzene, 11.9 mL of sulfuric acid, and 0.8 g of paraformaldehyde were mixed together, and the resulting mixture stirred to allow dissolution, to prepare 30 mL of a reaction liquid. In this reaction liquid, 1 g of the fibrous carrier A was immersed, and the reaction allowed to proceed for 1 hour while the reaction liquid was kept at 50° C. Subsequently, the reacted fiber was removed from the reaction liquid, and immersed in 40 mL of nitrobenzene for washing. The fiber was then immersed in methanol for washing and further immersed in water for washing to obtain a protein-adsorbing fiber (hereinafter referred to as "protein-adsorbing fiber J"). Table 1 shows the structure in which aromatic rings contained in the protein-adsorbing fiber J are linked to each other through the functional group.

(3) Preparation of Columns Having Protein-adsorbing Fibers as Adsorptive Carriers:

Polypropylene-polyethylene copolymer columns (40 mm diameter×133 mm length; volume of the adsorptive-fiber-packed portion, 40 cm$^3$) were packed with 54 g of each of the adsorptive fibers A to J. Subsequently, the columns were filled with water for injection (Otsuka Pharmaceutical Co., Ltd.), and then autoclaved to obtain columns containing the protein-adsorbing fibers A to J, respectively, as adsorptive carriers (hereinafter referred to as "columns A to J").

2. Measurement Method:

(1) Confirmation of Aromatic Rings and Structures Represented by Formula (I)

The aromatic rings and the structures represented by Formula (I) in the protein-adsorbing fibers A to J were identified based on $^1$H-NMR spectra. That is, each of the protein-adsorbing fibers A to J was dissolved in deuterated chloroform, and $^1$H-NMR spectra (TMS standard) were obtained using a nuclear magnetic resonance apparatus (JOEL RESONANCE Inc.) (resonant frequency, 270 MHz). Based on the $^1$H-NMR spectra obtained, structures represented by Formula (I) were identified according to relationships between proton positions and chemical shifts.

6.0 to 8.0 ppm: protons of aromatic rings
5.0 to 6.0 ppm: protons at the cross-linking points in the structures represented by Formula (I)
1.0 to 2.5 ppm: protons of the polystyrene backbone In addition, based on the $^1$H-NMR spectrum data, the ratio of the number of aromatic rings contained in each structure represented by Formula (I) to the total number of aromatic rings was calculated according to Equation (1).

Ratio (%)=(peak integral value at 5.0 to 6.0 (ppm))/
{(peak integral value at 6.0 to 8.0 (ppm))+(peak
integral value at 1.0 to 2.5 (ppm))}×⅕×100    (1)

(2) Measurement of Water Absorption Percentage:

To investigate the swelling properties of the protein-adsorbing fibers A to J, the water absorption percentage was measured according to the method described below. That is, a fibrous carrier cut into a 4 cm square shape was immersed in water for not less than 24 hours, and then sandwiched between two sheets of Kim Towel (manufactured by Nippon Paper Crecia Co., Ltd.) to sufficiently remove water, followed by measuring the weight before drying. Subsequently, the fibrous carrier was dried at normal temperature under vacuum for not less than 24 hours, and then the weight after drying was measured. The water absorption percentage was calculated according to Equation (2).

Water absorption percentage (%)={(weight of
adsorptive fibrous carrier before drying)–
(weight of adsorptive fibrous carrier after drying)}/(weight of adsorptive fibrous carrier
before drying)    (2)

(3) Measurement of IL-6 Adsorption Capacity

For each of the protein-adsorbing fibers A to J, the IL-6 concentration in the solution was measured by ELISA before and after adsorption reaction, and the adsorption rate calculated according to Equation (3). That is, four sheets of each of the protein-adsorbing fibers A to J, prepared by cutting into a disc shape having a diameter of 6 mm, were placed in a polypropylene container. To this container, 1.1 mL of fetal bovine serum (hereinafter referred to as FBS) prepared such that it contains human native IL-6 (Kamakura Techno-Science, Inc.) at 10,000 pg/mL was added, and the content of the container mixed by inversion for 2 hours in an incubator at 37° C. After removing the adsorptive fibrous carrier from the container, the residual concentration of IL-6 in the solution was measured using a commercially available human IL-6 ELISA kit (Kamakura Techno-Science, Inc.), and the IL-6 adsorption rate calculated according to Equation (3).

IL-6 adsorption rate (%)={(IL-6 concentration before
incubation)–(IL-6 concentration after incubation)}/(IL-6 concentration before incubation)×
100    (3)

(4) Measurement of Number of Insoluble Particulates:

The measurement was carried out by referring to General Tests, Processes and Apparatus 6.07 Insoluble Particulate Matter Test for Injections (Method 1. Light Obscuration Particle Count Test; pp. 1-2), published in The 15th Edition of the Japanese Pharmacopoeia (The Ministry of Health, Labour and Welfare Ministerial Notification No. 285; Mar. 31, 2006). By referring to Packaged Freights—Method of Vibration Test (JIS Z 0232), each column was vibrated horizontally and vertically for 1 hour each. The column after the vibration was connected to a commercially available blood circuit for artificial kidneys, and washed using 2 L of physiological saline at a flow rate of 100 mL/minute. The physiological saline was filtered through a filter with a pore size of 0.3 μm before use. The filtered physiological saline was introduced into the above product using a pump at a flow rate of 50 mL/minute for 1 hour, and 1 L of the discharged liquid collected every 20 minutes, a total of three times (total amount, 3 L). To a liquid-borne particle counter, 300 mL of each obtained sample of the discharged liquid was supplied for measurement of particulates. The total number of particulates detected during the 1 hour of feeding (particulates/mL) was calculated. In terms of the number of particulates detected during the 1 hour of liquid transfer, when the total number of particulates having a size of not less than 5 μm was not more than 0.5 particulate/mL and, at the same time, the total number of particulates having a size of not less than 25 μm was not more than 0.2 particulate/mL, the amount of particulates was judged to be small.

According to (2) the method of measuring the water absorption percentage and (3) the method of measuring the IL-6 adsorption capacity described above, the protein-adsorbing fibers A to J were evaluated. In addition, according to (4) the measurement test method for the number of insoluble particulates described above, the columns A to J were evaluated. The results of measurement of the water absorption percentage, the IL-6 adsorption capacity, and the number of insoluble particulates are shown in Table 2.

We found according to the results shown in Table 2 that the protein-adsorbing fibers A to E, wherein aromatic rings in the polymers are covalently linked to each other through structures represented by Formula (I), and the water absorption percentage is 1.2% to 49.7%, not only show high cytokine-removing performances with IL-6 adsorption rates of not less than 53.3%, but also enable reduction of generation of insoluble particulates (Examples 1 to 5).

On the other hand, the protein-adsorbing fiber F, wherein aromatic rings in the polymer are covalently linked to each other through a structure represented by Formula (I), but the water absorption percentage is 54.3%, exhibited a low cytokine-removing perfomiance with an IL-6 adsorption rate of 5.0%, although generation of insoluble particulates was suppressed (Comparative Example 1). The protein-adsorbing fiber G, wherein aromatic rings in the polymer are covalently linked to each other through a structure represented by Formula (I), but the water absorption percentage is 0.5%, exhibited a low cytokine-removing performance with an IL-6 adsorption rate of 3.0%, although generation of insoluble particulates was suppressed (Comparative Example 2). The protein-adsorbing fiber H, wherein aromatic rings in the polymer are covalently linked to each other through a structure represented by Formula (I), but the water absorption percentage is 0.8%, had a low cytokine-removing performance with an IL-6 adsorption rate of 7.5%, although generation of insoluble particulates was suppressed (Comparative Example 3). The protein-adsorbing fiber I, wherein the water absorption percentage is 46.4%, but aromatic rings in the polymer are not covalently linked to each other through a structure represented by Formula (I), exhibited a high level of generation of insoluble particulates, although it had a high cytokine-removing performance with an IL-6 adsorption rate of 60.2% (Comparative Example 4). The protein-adsorbing fiber J, wherein aromatic rings in the polymer are not covalently linked to each other through a structure represented by Formula (I), and the water absorption percentage is as low as 0.6%, exhibited a high level of generation of insoluble particulates, and a low cytokine-removing performance with an IL-6 adsorption rate of 7.0% (Comparative Example 5).

TABLE 1

| | Structural unit of protein-adsorbing fiber |
|---|---|
| Protein-adsorbing fiber A-C, F, G | 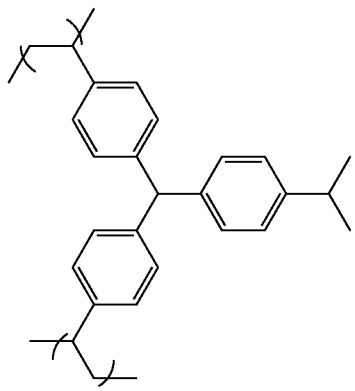 |
| Protein-adsorbing fiber E | 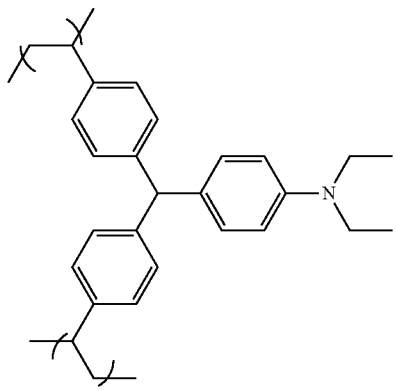 |
| Protein-adsorbing fiber D | 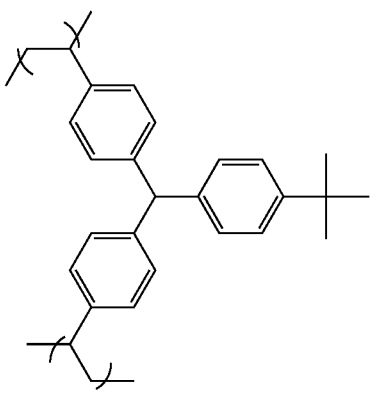 |

TABLE 1-continued

| | Structural unit of protein-adsorbing fiber |
|---|---|
| Protein-adsorbing fiber H | 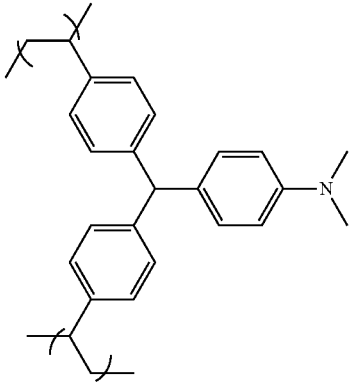 |
| Protein-adsorbing fiber I | 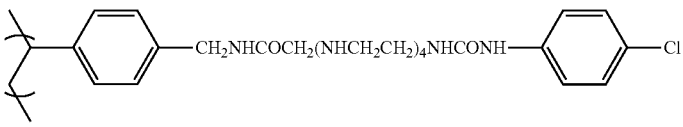 |
| Protein-adsorbing fiber J | 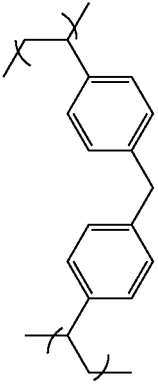 |

TABLE 2

| | Example 1 | Example 2 | Example 3 | Example 4 | Example 5 |
|---|---|---|---|---|---|
| Fibrous carrier used | Protein-adsorbing fiber A | Protein-adsorbing fiber B | Protein-adsorbing fiber C | Protein-adsorbing fiber D | Protein-adsorbing fiber E |
| Ratio of the number of aromatic rings contained in the structure represented by Formula (I) to the total number of aromatic rings contained in the fiber [%] | 22.2 | 4.3 | 68.5 | 45.9 | 12.2 |
| Water content [%] | 24.2 | 48.4 | 1.2 | 28.9 | 49.7 |
| IL-6 adsorption rate [%] | 80.7 | 69.1 | 53.3 | 74.3 | 69.6 |
| Eluted material [number/mL] Particulates: >5 μm 0-20 min | 0.01 | 0.01 | 0.01 | 0.01 | 0.01 |
| 20-40 min | 0.01 | 0.01 | 0.01 | 0.01 | 0.01 |
| 40-60 min | 0.01 | 0.01 | 0.01 | 0.01 | 0.01 |
| >25 μm 0-20 min | 0.01 | 0.01 | 0.01 | 0.01 | 0.01 |
| 20-40 min | 0.01 | 0.01 | 0.01 | 0.01 | 0.01 |
| 40-60 min | 0.01 | 0.01 | 0.01 | 0.01 | 0.01 |

| | Comparative Example 1 | Comparative Example 2 | Comparative Example 3 | Comparative Example 4 | Comparative Example 5 |
|---|---|---|---|---|---|
| Fibrous carrier used | Protein-adsorbing fiber F | Protein-adsorbing fiber G | Protein-adsorbing fiber H | Protein-adsorbing fiber I | Protein-adsorbing fiber J |

TABLE 2-continued

| | | | | | | | |
|---|---|---|---|---|---|---|---|
| Ratio of the number of aromatic rings contained in the structure represented by Formula (I) to the total number of aromatic rings contained in the fiber [%] | | | 0.8 | 74.5 | 82.5 | 0 | 0 |
| Water content [%] | | | 54.3 | 0.5 | 0.8 | 46.4 | 0.6 |
| IL-6 adsorption rate [%] | | | 5.0 | 3.0 | 7.5 | 60.2 | 7.0 |
| Eluted material [number/mL] | Particulates: >5 μm | 0-20 min | 0.01 | 0.01 | 0.01 | 163 | 64 |
| | | 20-40 min | 0.01 | 0.01 | 0.01 | 6.49 | 3.54 |
| | | 40-60 min | 0.01 | 0.01 | 0.01 | 1.91 | 0.88 |
| | >25 μm | 0-20 min | 0.01 | 0.01 | 0.01 | 0.58 | 0.56 |
| | | 20-40 min | 0.01 | 0.01 | 0.01 | 0.06 | 0.03 |
| | | 40-60 min | 0.01 | 0.01 | 0.01 | 0.06 | 0.03 |

In each Example, a nonaromatic polymer was used except for the polymer corresponding to the polymer B. Thus, the total number of aromatic rings contained in the fiber is the same as the number of aromatic rings in the polymer B.

INDUSTRIAL APPLICABILITY

The fiber for protein adsorption can be favorably used for adsorptive removal of proteins such as $\beta_2$-MG and cytokines from protein-containing liquids to be processed such as blood, body fluids from living bodies, and drainages from living bodies. The fiber for protein adsorption can also be used for columns for protein adsorption for treatment of diseases that require removal of a particular substance to be adsorbed such as extracorporeal circulation columns for removal of proteins including $\beta_2$-microglobulin, cytokines, and autoimmune antibodies; and lipid-protein complexes including low-density lipoproteins.

The invention claimed is:

1. A fiber for protein adsorption,
wherein said fiber has a water absorption percentage of 1 to 50%; and
said fiber comprises a polymer containing as repeat units an aromatic hydrocarbon and/or a derivative thereof, wherein part of aromatic rings contained in said repeat units are cross-linked through a structure represented by Formula (I):

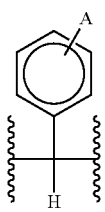

(I)

wherein A is selected from the group consisting of an aliphatic group, aromatic group and amino group, and each wavy line represents a position bound to an aromatic ring.

2. The fiber according to claim 1, wherein, in said formula, A represents Formula (A-1), (A-2), or (A-3):

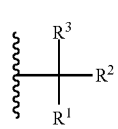

(A-1)

(A-2)

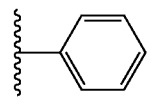

(A-3)

wherein $R^1$ to $R^5$ each independently represent a hydrogen atom or a $C_1$-$C_{10}$ hydrocarbon group, and each wavy line represents a binding position.

3. The fiber according to claim 1, wherein said polymer is a polymer selected from the group consisting of polystyrene, polysulfone, and derivatives thereof.

4. The fiber according to claim 1, wherein the single yarn diameter of said fiber is 0.1 to 1000 μm.

5. The fiber according to claim 1, wherein a number of aromatic rings in Formula (I) with respect to a total number of aromatic rings contained in said cross-linked polymer is 4 to 70%.

6. The fiber according to claim 1, adapted for cytokine adsorption.

7. A column for protein adsorption comprising, as an adsorptive carrier, the fiber according to claim 1.

8. The fiber according to claim 2, wherein said polymer is a polymer selected from the group consisting of polystyrene, polysulfone, and derivatives thereof.

9. The fiber according to claim 2, wherein the single yarn diameter of said fiber is 0.1 to 1000 μm.

10. The fiber according to claim 3, wherein the single yarn diameter of said fiber is 0.1 to 1000 μm.

11. The fiber according to claim 2, wherein a number of aromatic rings in Formula (I) with respect to a total number of aromatic rings contained in said cross-linked polymer is 4 to 70%.

12. The fiber according to claim 3, wherein a number of aromatic rings in Formula (I) with respect to a total number of aromatic rings contained in said cross-linked polymer is 4 to 70%.

13. The fiber according to claim 4, wherein a number of aromatic rings in Formula (I) with respect to a total number of aromatic rings contained in said cross-linked polymer is 4 to 70%.

14. The fiber according to claim 2, adapted for cytokine adsorption.

15. The fiber according to claim 3, adapted for cytokine adsorption.

16. The fiber according to claim 4, adapted for cytokine adsorption.

17. The fiber according to claim 5, adapted for cytokine adsorption.

18. A column for protein adsorption comprising, as an adsorptive carrier, the fiber according to claim 2.

19. A column for protein adsorption comprising, as an adsorptive carrier, the fiber according to claim 3.

20. A column for protein adsorption comprising, as an adsorptive carrier, the fiber according to claim 4.

* * * * *

UNITED STATES PATENT AND TRADEMARK OFFICE
CERTIFICATE OF CORRECTION

PATENT NO. : 9,982,369 B2
APPLICATION NO. : 15/511185
DATED : May 29, 2018
INVENTOR(S) : Kasuya et al.

Page 1 of 1

It is certified that error appears in the above-identified patent and that said Letters Patent is hereby corrected as shown below:

In the Specification

In Column 3
At Line 9, please change "I3$_2$" to -- $\beta_2$ --.

Signed and Sealed this
Second Day of October, 2018

Andrei Iancu
*Director of the United States Patent and Trademark Office*